United States Patent [19]
Bales et al.

[11] Patent Number: 5,466,397
[45] Date of Patent: Nov. 14, 1995

[54] NONLINEAR OPTICALLY ACTIVE PYRAZOLINES AND POLYMERIC COMPOSITIONS CONTAINING MOIETIES DERIVED THEREFROM

[75] Inventors: Stephen E. Bales; David J. Brennan; Robert J. Gulotty, Jr.; Muthiah N. Inbasekaran; Michael N. Mang; Mark D. Newsham, all of Midland, Mich.

[73] Assignee: The Dow Chemical Company, Midland, Mich.

[21] Appl. No.: 159,010

[22] Filed: Nov. 29, 1993

[51] Int. Cl.$^6$ ................... F21V 9/00; C08F 2/46
[52] U.S. Cl. ............ 252/582; 252/587; 522/167; 522/170
[58] Field of Search ................... 252/582, 587, 252/589; 359/326, 328; 522/166, 167, 170

[56] References Cited

U.S. PATENT DOCUMENTS

| | | | |
|---|---|---|---|
| 3,395,329 | 7/1968 | Rentzepis . | |
| 3,431,484 | 3/1969 | Pao et al. | 321/69 |
| 3,858,124 | 12/1974 | Bass et al. | 332/7.51 |
| 4,994,209 | 2/1991 | Okazaki | 252/582 |
| 5,106,936 | 4/1992 | Gulotty et al. | 528/125 |
| 5,112,934 | 5/1992 | Kester et al. | 528/99 |
| 5,173,546 | 12/1992 | Kester et al. | 525/504 |
| 5,187,237 | 2/1993 | Nordmann et al. | 525/326.2 |
| 5,208,299 | 5/1993 | Bales et al. | 525/437 |

FOREIGN PATENT DOCUMENTS

| | | |
|---|---|---|
| 0406888A2 | 1/1991 | European Pat. Off. . |
| 0445864A1 | 9/1991 | European Pat. Off. . |
| 0474402A2 | 3/1992 | European Pat. Off. . |
| 920341 | 3/1992 | WIPO . |

OTHER PUBLICATIONS

Swalen et al., "Poled Epoxy Polymers for Optoelectronics", Organic Molecules for Nonlinear Optics and Photonics, J. Messier et al. editors, vol. 194, pp. 433–445 (1991).

Swalen et al., "Organic Nonlinear Optical Materials and Their Device Applications for Frequency Doubling Modulation, and Switching", SPIE, Nonlinear Optical Properties of Organic Materials III, vol. 1337, pp. 2–11 (1990).

Twieg et al., "Nonlinear Optical Epoxy Polymers with Polar Tolan Chromophores", Mol. Cryst. Liq. Cryst., vol. 217, pp. 19–24 (1992).

Jungbauer et al., "Highly Efficient and Stable Nonlinear Optical Polymers via Chemical Crosslinking Under Electric Field", Appl. Phys. Lett., v. 56, No. 26, pp. 2610–2612 Jun. 25, 1990.

Eich et al., "Novel Second-Order Nonlinear Optical Polymers via Chemical Cross-linking-induced Vitrification Under Electric Field" J. Appl. Phys., v. 66, #7, pp. 3241–3247, Oct. 1, 1989.

Hubbard et al., "Poled Polymeric Nonlinear Optical Materials. Enhanced Second Harmonic Generation Temporal Stability of Epoxy-Based Matrices Containing a Difunctional Chromophoric Co-Monomer", Chem. Mater., vol. 4, pp. 965–968 (1992).

Hubbard et al., "Poled Polymeric Nonlinear Optical Materials. Enhanced Second Harmonic Generation Stability of Cross-linkable Matrix/Chromophore Ensembles", Chemistry of Materials, v. 1, #2, pp. 167–169, Mar./Apr. 1989.

*Primary Examiner*—Philip Tucker

[57] ABSTRACT

Disclosed are compounds containing substituted pyrazoline which exhibit nonlinear optical activity on orientation and to oriented polymeric compositions comprising moieties derived therefrom in the backbone of the polymer. Also disclosed are the processes for making the oriented polymeric composition of the invention.

19 Claims, No Drawings

NONLINEAR OPTICALLY ACTIVE PYRAZOLINES AND POLYMERIC COMPOSITIONS CONTAINING MOIETIES DERIVED THEREFROM

The present invention relates to substituted pyrazolines exhibiting nonlinear optical properties on orientation and to oriented nonlinear optical polymeric compositions containing moieties derived therefrom.

BACKGROUND OF THE INVENTION

Information may be more rapidly processed and transmitted using optical as opposed to electrical signals. Optical signals can be used to enhance the performance of electronic processors. For example, electronic wires interconnecting integrated circuits (ICs) can be replaced with optical interconnects and the information processed with IC driven electro-optic (EO) modulators. Optical signals in fiber optic communications can be encoded on the optical carrier using EO modulators. In both of these processes, nonlinear optical materials with second-order nonlinear optical activity are necessary to effect modulation of the light signal.

Nonlinear optical materials can also be used for frequency conversion of laser light. Such a conversion is desirable in many applications. For example, optical memory media are presently read using 830 nm light from diode lasers. The 830 nm light wavelength limits the spot sizes which can be read and hence the density of data stored on the optical memory media. In fiber optic communications, light wavelengths of 1.3 µm or 1.5 µm are desirable due to the low transmission losses of glass fiber at those wavelengths. However, those wavelengths are too long for detection by Si based detectors. It is desirable to frequency double the 1.3 µm or 1.5 µm wavelengths to 650 nm or 750 nm wavelengths where Si based detectors could be used.

Nonlinear optical materials which have been used in electro-optic devices have in general been inorganic single crystals such as lithium niobate ($LiNbO_3$) or potassium dihydrogen phosphate (KDP). More recently, nonlinear optical materials based on organic molecules, and in particular polar aromatic organic molecules have been developed.

Organic nonlinear optical materials have a number of potential advantages over inorganic materials. First, organic nonlinear optical materials have higher NLO activity on a molecular basis. Organic crystals of 2-methyl-4-nitroaniline have been shown to have a higher nonlinear optical activity than that of $LiNbO_3$. Second, the nonlinear optical activity of the organic materials is related to the polarization of the electronic states of the organic molecules, offering the potential of very fast switching times in EO devices. The time response of the organic nonlinear optical system to a light field is on the order of 10 to 100 femtoseconds. In contrast, a large fraction of the second order polarizability in the inorganic crystals in EO applications is due to lattice vibrations in the crystal, slowing the time-response of the materials. In addition, the low dielectric constant of the organic materials (e.g., 2-5 Debye at 1 MHz) compared to the inorganic materials (e.g., 30 Debye at 1 MHz) enables higher EO modulator frequencies to be achieved for a given power consumption. Third, the organic materials can be easily fabricated into integrated device structures when used in polymer form.

One of the promising and recent approaches to making stable nonlinear optically active organic materials involves forming highly crosslinked networks where polar molecules are polymerized directly into the polymer reagent matrix during the poling process. Eich et al., *J. Appl. Phys.*, 66(7), Oct. 1, 1989, pp 3241–3247, discloses the preparation of nonlinear optically active crosslinked polymer networks from the reaction of epoxides, with and without nonlinear optic dye moieties, and NLO active di- and tri-functional amines, in which the NLO amine is attached to the network by two chemical bonds. Jungbauer et al., *Appl. Phys. Lett.*, 56(26), Jun. 25, 1990, pp 2610–2612, discloses a crosslinked polymer network by reacting a diepoxide with a trifunctional amine in which the NLO active group is attached to the crosslinked polymer network by only one chemical bond. European Patent Application No. 0 474 402 A2 discloses multi-functional chromophore containing polymerizable compounds which are capable of being polymerized into a crosslinked network.

Another approach to making nonlinear optically active organic materials involves side chain liquid crystalline polymers, with the NLO chromophore in the side chain as disclosed in U.S. Pat. Nos. 4,855,376; 4,948,532 and 4,933,112.

Still another approach is disclosed in Allen et. al., *J. Appl. Phys.*, 64(5), Sep. 1, 1988, pp 2583–2589, and involves making nonlinear optically active, single crystal structures of highly conjugated molecules based on substituted dihydropyrazoles.

There is a continuing effort to develop new nonlinear optical polymers with increased nonlinear optical susceptibilities and enhanced stability of nonlinear optical effects.

It is an object of this invention to make thermoplastic and thermoset polymeric compositions incorporating organic molecular structures which exhibit NLO activity upon orientation. It is an additional object of the present invention that the polymers comprising the NLO molecular structures or chromophores have relatively high glass transition temperatures.

It is still a further object of the invention to provide organic polymeric materials with larger and thermally more stable second order nonlinear optical properties than presently used organic electrooptic materials.

SUMMARY OF THE INVENTION

It has now been discovered that substituted pyrazolines provide compounds which exhibit nonlinear optical activity upon orientation. The compounds of the invention when incorporated in the backbone of polymers provide polymeric compositions which have rigid backbones and exhibit thermally stable nonlinear optical activity on orientation.

In one embodiment, the invention is a compound corresponding to Formula I:

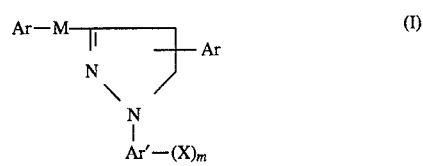

or to Formula II:

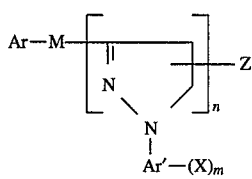

(II)

wherein Ar is independently at each occurrence an aromatic hydrocarbyl or heterocylic radical substituted with from zero to three polymerizable OR groups and optionally substituted with inert substituents; R is a hydrogen, alkylepoxy, or an epoxy; Ar' is an aromatic hydrocarbyl or heterocyclic radical containing up to 30 non-hydrogen atoms; X is an electron withdrawing group; M is a covalent bond or a divalent conjugated group; Z is a divalent or a trivalent aromatic carbocyclic or heterocyclic radical or a substituted divalent or a trivalent aromatic carbocyclic or heterocyclic radical containing up to 30 non-hydrogen atoms, or a covalent bond; n is 2 or 3; and m is an integer of 1 to 3; provided there are at least two aromatically substituted OR groups present in the compound.

In another embodiment, the invention relates to a compound corresponding to Formula I or Formula II exhibiting nonlinear properties when oriented by an external field.

In yet still another embodiment, the present invention relates to a nonlinear optical medium comprising an oriented polymeric composition having moieties derived from a compound corresponding to Formula I or to Formula II.

In yet still another embodiment, the present invention relates to a process for preparing an oriented polymeric composition, comprising applying an external field to a polymeric composition having moieties derived from a compound corresponding to Formula I or to Formula II.

In yet still another embodiment, the present invention relates to a process for preparing an oriented polymeric composition, comprising substantially simultaneously applying an external field and thermally annealing the reaction product of at least one compound corresponding to Formula I or to Formula II with at least one compound capable of copolymerizing therewith, for a period of time sufficient to form a composition having nonlinear optical properties.

In yet still another embodiment, the present invention is a device comprising the nonlinear optical compound corresponding to Formula 1 or to Formula II or an oriented polymer composition of the invention.

DETAILED DESCRIPTION OF THE INVENTION

The term "orientation" as used herein refers to the alignment of molecular dipoles upon the application of an external field to a molecule or moieties derived therefrom according to the methods described herein, or by some other means, such that the molecule, or the moieties derived therefrom exhibit nonlinear optical activity.

The phrase "oriented polymeric composition" refers to the polymeric composition following orientation as described above.

The term "external field" as used herein refers to an electric, magnetic or mechanical stress field which is applied to a substrate of mobile organic molecules to induce dipolar alignment of the molecules parallel to the field.

The phrase "aromatically substituted" herein refers to substituents that are directly attached to a carbocyclic or heterocyclic aromatic ring represented by radicals Ar and Ar'.

The term "inert" as used herein means a substituent which is inert in the condensation reactions which are employed to prepare the polymeric compositions.

The term "electron donating" as used herein refers to organic substituents which contribute n-electrons to a conjugated electronic structure.

In the compound of the invention represented by Formula (I) or (II), there are at least two aromatically substituted polymerizable OR group present, wherein R is a hydrogen, an epoxy, or an alkylepoxy. The alkyl group in alkylepoxy is a lower akyl group containing 3–6 carbon atoms. The "OR" group acts as a polymerizable group capable of undergoing condensation polymerization processes used to obtain the polymeric compositions of the invention. The "OR" group can also function as an electron donating group.

The "Ar" radical in the compounds of the invention represented by Formula (I) or Formula (II) may be optionally further substituted with inert substituents. Illustrative of the inert substituents include R' or OR' wherein R' is a $C_1$–$C_{20}$ hydrocarbyl radical. OR' functions as an electron donating group, when present in the compounds of the invention.

Illustrative of Ar radicals include:

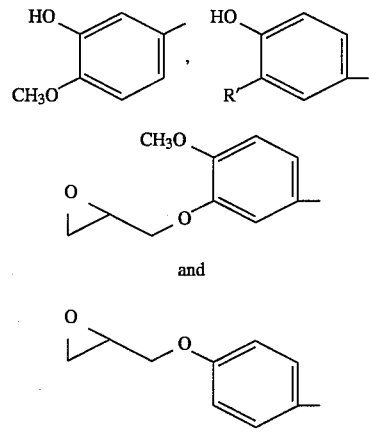

and

The compounds of the invention contain at least one aromatically substituted electron withdrawing group represented by X, attached to a carbocyclic or heterocyclic aromatic radical represented by Ar', which may optionally be further substituted with more electron withdrawing groups or above-described inert substituents.

Illustrative of Ar' radicals suitable for the purpose of this invention include: phenyl, naphthalene, anthracene, biphenyl, pyridyl, and the like.

The term "electron withdrawing", as employed herein, refers to any substituent which attracts the electrons from a conjugated electron structure, thereby providing a polarized resonating structure. A quantification of the level of electron-withdrawing capability is given by the Hammett $\sigma$ (sigma) constant. This well known constant is described in many references, for instance, J. March, *Advanced Organic Chemistry*, (McGraw Hill Book Company, New York, 1977 edition) pp. 251–259. The Hammett constant values are negative for electron donating groups ($\sigma_p$=–0.66 for $NH_2$) and positive for electron withdrawing groups ($\sigma_p$=0.78 for a nitro group, $\sigma_p$ indicating para substitution.)

Preferred electron withdrawing groups are those having a

Hammett constant of ($\sigma_p$) at least 0.50, and more preferably at least 0.60.

Illustrative of the electron withdrawing groups useful in the present invention include: —$NO_2$, —$SO_2R''$, —$SO_2CH_2F$, —$SO_2CHF_2$, —$SO_2CF_3$, —$S(NSO_2CF_3)CF_3$, —$CF_3$, —$CO_2R''$, —$COCF_3$, cyano, cyanovinyl, dicyanovinyl, and tricyanovinyl, wherein $R''$ is hydrogen or a $C_1$ to $C_{20}$ hydrocarbyl radical.

The term "conjugated" group, as employed herein refers to a moiety containing alternating double or triple bonds which has the ability to transfer electronic charge. Conjugated moieties generally include groups which have, for example, a hydrocarbyl diradical comprising a single aromatic ring, multiple fused rings or multiple aromatic rings linked by carbon-carbon, carbon-nitrogen, or nitrogen-nitrogen double bonds. The conjugated groups may be substituted with pendant radicals such as alkyl, aryl, cyano, halo and nitro groups.

In Formula (I) or (II), examples of the divalent conjugated groups represented by M include: —C≡C—, —$CR''$=$CR''$—, —$CR''$=$CR''$—$CR''$=$CR''$—, —$CR''$=N—, —N=$CR''$—, and —N=N—, wherein $R''$ is as defined above.

In Formula (I) or (II), examples of divalent or trivalent radicals represented by Z include those derived from phenyl, naphthalene, anthracene, biphenyl and the like.

The pyrazolines of the present invention can be produced by a suitably catalyzed reaction of a desired hydrazine with a desired unsaturated carbonyl compound. A catalyst such as mineral acid is generally employed to increase the rate of the reaction. Acetic acid is suitably employed as a catalyst and as a solvent. For the vinylpyrazolines, the preferred acid catalyst is hydrochloric acid. The reaction may be carried out in the presence of other solvents such as ethanol, methanol and the like. The reactants are added to a suitable solvent and brought to boiling in the presence of the acid catalyst. Upon cooling, the desired pyrazoline is precipitated and recovered by filtration. The pyrazolines can be crystallized from a suitable solvent such as dimethylformamide (DMF), ethanol, DMF-ethanol mixture and the like.

Suitable hydrazines for the purpose of this invention include those represented by Formula:

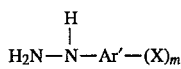

wherein Ar', m and X are as defined above.

Illustrative but not limiting of the hydrazines include 4-nitrophenylhydrazine, 2,4-dinitrophenylhydrazine, 4-(methylsulfonyl)phenylhydrazine, and 4-(tricyanovinyl)phenylhydrazines.

Suitable unsaturated carbonyl compound include those represented by Formula:

or by Formula:

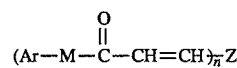

In the Formulae, at least one Ar is substituted with at least one OH group directly attached thereto. Ar, M and Z are as defined above.

The unsaturated carbonyl compounds are prepared by the condensation of an aldehyde and a ketone containing a hydrogens catalyzed by a suitable base, as taught by E. P. Kohler and H. M. Chadwell (*Organic Synthesis Collective Volume* 1, second edition, p. 78). The preferred catalysts are inorganic bases such as sodium or potassium hydroxide and an organic base such as piperidine. The preferred solvents are ethanol, methanol, or ethanol-water mixtures. The condensation reaction proceeds at room temperature in the case of inorganic bases and at reflux temperatures when piperidine is employed as catalyst.

Illustrative but not limiting of the unsaturated carbonyl compounds include 1,5-bis-(3-hydroxy-4-methoxyphenyl)-1,4-pentadien-3-one, and chalcones which are obtained by reacting acetovanillone and terephthaldehyde or isophthaldehyde.

The hydroxy pyrazolines obtained from the above-described carbonyl compounds and the pyrazolines is reacted with an excess of epoxide such as epihalohydrin, followed by dehydrohalogenation to obtain the epoxy pyrazolines containing at least two epoxy or alkylepoxy groups. The alkyl group in the alkylepoxy is represented by a $C_1$–$C_{20}$ hydrocarbyl group.

The compounds of the invention exhibit nonlinear optical properties upon orientation. The compounds of this invention are preferably incorporated as recurring moieties forming at least part of the backbone of the polymeric compositions, which upon orientation exhibit nonlinear optical properties.

The incorporation of the NLO active moieties derived from the compounds of the invention has a number of advantages. High levels of NLO chromophore functionalization can be achieved without increasing the scattering losses of waveguides fabricated from the polymer. The addition of the groups which add to the NLO activity of the polymer do not plasticize the polymer and lower the polymer $T_g$. In fact, such modifications can raise the polymer $T_g$. Furthermore, the fact that the NLO chromophore is inherent to the polymer backbone increases the orientational stability of the NLO chromophores, reducing the temporal decay of the NLO activity with time. Thus, polymers containing this monomer have the advantage of high $T_g$ and increased orientation stability when fabricated into a nonlinear optical film or other NLO article in comparison to other NLO polymers.

The polymers of this invention may be homopolymers containing moieties derived from the compounds of the invention in the backbone of the polymer, or copolymers having at least one other comonomer copolymerizable therewith.

The polymeric compositions of the invention are obtained by condensation polymerization methods known to those skilled in the art. See, for example, *Principles of Polymerization*, George Odian, Wiley, New York, 1981. Preferably, the polymerization is carried out by step-growth polymerization. It is well known in the art that step-growth polymerizations can provide high molecular weight polymers when the monomers are difunctional and present in about 1:1 stoichiometric ratio, and low molecular weight polymers when the stoichiometric ratio of the respective monomer is less than about 1:1.

The desired stoichiometry of the reaction may be obtained by either altering the mole ratios of the respective monomers in the reaction mixture or by adding monofunctional encapping agents, which act as chain terminators. The end groups in the polymer are statistically dependent upon the monomer present in stoichiometric excess in the initial polymerization mixture.

The polymers of the invention may be oligomers, thermoplastic, or thermoset polymers and can be obtained by proper stoichiometry, proper selection of monomers, and optional endcapping agent as taught in Malcolm P. Stevens, *Polymer Chemistry*, Oxford University Press, 1990, relevant portions of which are incorporated herein by reference.

Thermoplastic Polymeric Compositions

The thermoplastic polymeric compositions, for example, are represented by polyesters, polycarbonates, polyestercarbonates, polyethers, poly(hydroxyethers), and poly(aminoethers).

Suitable monomers for copolymerization with the compounds of the inventions include: diepoxides, diglycidyl ethers, diphenols, dithiols, diacids and difunctional amines, compounds containing two active amine hydrogens, acid chlorides, and the like.

The mole ratio of the monomer to the compound of Formula (I) or Formula (II), to be employed, varies in range from 90:10 to 10:90. Preferably, the mole ratio varies from 30:70 to 70:30.

Diphenols which can be employed in the practice of the present invention include the bisphenols described in U.S. Pat. Nos. 5,115,075; 4,480,082 and 4,438,254, and in copending U.S. applications Ser. No. 800,340, filed on Nov. 26, 1991, and Ser. No. 884,673, filed on May 18, 1992, all of which are incorporated herein by reference. Preferred diphenols include 4,4'-isopropylidenebisphenol (bisphenol A), 4,4'-sulfonyldiphenol, 4,4'-oxydiphenol, 4,4'-methylenediphenol, 4,4'-thiodiphenol, 9,9-bis(4-hydroxyphenyl)fluorene, 4,4'-biphenol, 4,4'-dihydroxybenzophenone, hydroquinone, resorcinol, and 3,3',5,5'-tetrabromobisphenol A. More preferred phenols are 4,4'-isopropylidenebisphenol (bisphenol A), 9,9-bis(4-hydroxyphenyl)fluorene, hydroquinone, resorcinol, 4,4'-sulfonyldiphenol, 4,4'-thiodiphenol, 4,4'-oxydiphenol, and 4,4'-biphenol. Most preferred phenols are 4,4'-isopropylidenebisphenol (bisphenol A), 4,4'-sulfonyldiphenol, 4,4'-oxydiphenol, and 9,9-bis(4-hydroxy-phenyl)fluorene. The diphenols may include the hydroxy arylhydrazone of the invention.

Dithiols which can be employed in the practice of the present invention include those represented by the formula HS—R—SH, wherein R is a hydrocarbylene or a divalent aromatic moiety. Preferably, R is (1) alkylene or cycloalkylene which optionally contains a heteroatomic moiety such as oxygen, sulfur, sulfonyl, or sulfoxyl or (2) arylene which optionally contains a heteroatomic moiety and optionally substituted with alkyl, alkoxy, halo, nitro, cyano or cycloalkyl groups. More preferred dithiols include 1,4-butanedithiol, 1,5-pentanedithiol, mercaptoethyl ether, 1,6-hexanedithiol, and 4,4'-dimercaptodiphenyl ether (DMPE). The most preferred dithiol is DMPE. Dithiols and processes for preparing them are well known. See, for example, U.S. Pat. No. 3,326,981 and Sutter Scrutchfield, *Journal of The American Chemical Society*, 58, p. 54 (1936).

Dicarboxylic acids which can be employed in the practice of the present invention include 4,4'-biphenyldicarboxylic acid, 2,6-naphthalenedicarboxylic acid, isophthalic acid and terephtalic acid. Preferred diacids include isophthalic acid and terephthalic acid. Most preferred diacid is terephthalic acid.

Difunctional amines which can be employed in the practice of the present invention include amines having two reactive hydrogen atoms such as ethanolamine, propanolamine, 2-aminopropionamide, aniline, 4-hydroxyaniline, anisidine, benzylamine, piperazine and 2,5-dimethylpiperazine.

Diepoxides which can be employed in the practice of the present invention include the diglycidyl ethers of 9,9-bis(4-hydroxyphenyl)fluorene, hydroquinone, resorcinol, 4,4'-sulfonyldiphenol, 4,4'-thiodiphenol, 4,4'-oxydiphenol, 4,4'-dihydroxybenzophenone, tetrabromoisopropylidenebisphenol, 4,4'-biphenol, 4,4'-dihydroxybiphenylene oxide, bis(4-hydroxyphenyl)methane, α,α-bis(4-hydroxyphenyl)ethylbenzene, 2,6-dihydroxynaphthalene and 4,4'-isopropylidene bisphenol (bisphenol A). More preferred diglycidyl ethers are the diglycidyl ethers of 9,9-bis(4-hydroxyphenyl)fluorene, hydroquinone, resorcinol, 4,4'-sulfonyldiphenol, 4,4'-thiodiphenol, 4,4'-oxydiphenol, 4,4'-dihydroxybenzophenone, tetrabromoisopropylidenebisphenol, 4,4'-biphenol, 4,4'-dihydroxybiphenylene oxide, bis(4-hydroxyphenyl)methane, α,α-bis(4-hydroxyphenyl)ethyl-benzene, 2,6-dihydroxynaphthalene and 4,4'-isopropylidene bisphenol (bisphenol A). Most preferred diglycidyl ethers are the diglycidyl ethers of 4,4'-isopropylidene bisphenol (bisphenol A), 4,4'-sulfonyldiphenol, 4,4'-oxydiphenol, 4,4'-dihydroxybenzophenone, and 9,9-bis(4-hydroxyphenyl)fluorene. Diepoxides also include the epoxy arylhydrazones described above.

Methods of producing polycarbonates and polyestercarbonates are well-known in the prior art. Such methods are suitable for use in preparing the polymeric compositions of the present invention.

Suitable methods for preparing polycarbonate resins are set forth in U.S. Pat. Nos. 3,248,414; 3,153,008; 3,215,668; 3,187,065; 3,028,365; 2,999,846; 2,964,974; 2,970,137; 1,991,273; and 2,999,835; all of which are incorporated herein by reference. The polycarbonates of the present invention are prepared by the reaction of the dihydroxyaryl pyrazolines with a carbonate precursor. The carbonate precursor may be either a carbonyl halide, a diaryl carbonate or a bishaloformate. The carbonyl halides include carbonyl bromide, carbonyl chloride and mixtures thereof.

Similarly, methods of producing polyestercarbonates are known in the prior art. Exemplary of methods by which polyestercarbonates may be produced are those methods described in U.S. Pat. Nos. 3,169,121; 4,287,787; 4,156,069; 4,260,731; 4,330,662; 4,360,656; 4,374,973; 4,255,556; 4,388,455; 4,355,150; 4,194,038; 4,238,596; 4,238,597; 4,252,939; 4,369,303 and 4,105,633; and articles by Kolesnikov et al. published in *Vysokomol Soedin* as B9, 49 (1967); A9, 1012 (1967); A9, 1520 (1967); and A10, 145 (1968); all of which are incorporated herein by reference. Generally, the aforementioned processes involve the reaction of dihydroxyl containing compounds with phosgene or other suitable carbonate precursor or with a mixture of phosgene or other carbonate precursor and a dicarboxylic acid, acid anhydride or acid halide.

Methods of producing poly(hydroxy ethers) and polyethers are well known in the prior art and are suitable for use in forming the polymeric compositions of the present invention. Suitable methods for preparing poly(hydroxy ethers) are set forth in U.S. Pat. Nos. 2,602,075; 3,305,528; 4,647,648; and 5,089,588; in articles by Reinking, Barnabeo, and Hale published in *J. Appl. Poly m. Sci.*, 7, 2135–2160 (1963); and in the *Encyclopedia of Polymer Science and Technology*, 10, 111–122, all of which are incorporated herein by reference.

Poly(amino ethers) of the present invention are generally prepared by contacting the compound of this invention containing at least one epoxy group with an amine under conditions sufficient to cause the amine moieties to react with epoxy moieties to form a polymer backbone having amine linkages, ether linkages and pendant hydroxyl moieties.

Preferably, the mole ratio of the compound to that of the amine is between about 0.97 to about 1.03. Optionally, a capping agent may be added to the reaction mixture for minimizing the unreacted terminal epoxy groups in the poly(amino ether). Illustrative, but not limiting of suitable capping agents are t-butyl phenol, piperidine, and 2-hydroxyethyl piperazine.

Conditions employed in preparing the poly(amino ethers) of this invention are those conventionally employed in the reaction of diglycidyl ethers with amines to form amine linkages and pendant hydroxyl groups. Examples of such conditions are set forth in U.S. Pat. No. 3,317,471, which is hereby incorporated by reference in its entirety. In general, however, the process for preparing the polymers is carried out so that the unreacted epoxy groups in the finished poly(amino ether) are minimized. By minimizing the epoxy groups in the poly(amino ether), the essential thermoplastic character of the poly(amino ether) can be retained. This process for preparing the polymers is described in now allowed, commonly owned U.S. application Ser. No. 864,975, filed Apr. 7, 1992.

Thermoset Polymeric Compositions

The thermoset compositions of the invention can be obtained by curing at least one compound corresponding to Formula (I) or Formula (II) with at least one curing agent capable of reacting with the compound, by methods well known in the art.

Generally, the amounts of the compound of the invention and the curing agent employed herein are sufficient to provide a cured product. Usually the amounts of the compound and the curing agent which provide a ratio of equivalents of curing agent per epoxy group from about 0.5 to about 1.2; preferably from about 0.95 to about 1.05 are used herein.

The curing agents which can be employed herein include, for example, amines, acids or anhydrides thereof, biguanides, imidazoles, urea-aldehyde resins, melamine-aldehyde resins, phenolics, halogenated phenolics, sulfides and and combinations thereof. These and other curing agents are disclosed in Lee and Neville's *Handbook of Epoxy Resins*, McGraw-Hill Book Co., 1967. The curing agent may be a compound which exhibits a NLO response. Nonlinear optical active amine curing agents, and crosslinked epoxy polymers thereof, exhibiting nonlinear optical activity are described in the European Patent Application Nos. 0,436,115 A3; 0,430,143 A3; and 0,430,142 A3. Suitable curing agents, for example, include 4,4'-diaminodiphenyl sulfone, p-nitroaniline, nitrobenzyl amine, Disperse Orange, methyl nitroaniline, amino nitropyrimidine, 2-6-diamine 4-nitrotoluene, 5-nitrobenzotriazole and combinations thereof, bisphenol A, tetrabromobisphenol A, phenolformaldehyde novolac resins, halogenated phenolformaldehyde resins, hydrocarbonphenol resins and combinations thereof.

Preferably, the thermoset polymeric compositions are obtained by curing a compound of Formula I or Formula II containing at least two epoxy groups with an amine curing agent containing at least two active amine hydrogens. Most preferably, the compounds of the invention contain at least two glycidyl ether groups. The methods of curing and obtaining the thermoset compositions are described in European Patent Application 0 430 143 A3, relevant portions of which are incorporated herein by reference.

It may be advantageous to include commercially available epoxy resins to the polymerization mixture. Some commercial epoxy resins useful in the present invention include, for example, D.E.R.™ 331, D.E.R.™ 332, D.E.R.™ 383, D.E.R.™ 431, D.E.R.™ 736, D.E.R.™ 661, and Tactix™ 742, all commercially available from The Dow Chemical Company.

The thermoset polymeric compositions of the present invention are preferably prepared by making a prepolymer by melt or solution polymerization methods known in the art. The prepolymer is used to form a film by methods described hereinbelow. The film so obtained is cured to provide the crosslinked thermoset polymeric composition of the present invention.

The thermoset polymeric compositions can also be obtained by crosslinking the above-described oligomers and thermoplastic polymeric compositions by the techniques known in the art, and also taught in, for example, Malcolm P. Stevens, *Polymer Chemistry*, Oxford University Press, 1990, relevant portions of which have been incorporated herein by reference.

The oriented polymeric composition can be prepared by applying an external field to the polymeric compositions described above. The polymeric compositions of the present invention can be in the form of sheets, films, fibers or other shaped articles formed by conventional techniques. Generally, films are used in testing, electro-optic devices and waveguide applications.

Methods of fabricating films of NLO polymers and the methods of characterization of NLO activity are well known to those skilled in the art. Polymer films are typically fabricated by spin-coating or dip-coating a polymer solution onto a substrate. The substrate used depends on the poling method and method of characterization. For corona poling, a glass substrate such as a microscope slide is typically used. For parallel plate poling, a substrate with an electrically conductive surface is necessary, such as indium-tin-oxide (ITO) coated glass. The coated glass slides can be used directly for corona poling. The coated ITO slides for parallel plate poling require an electrically conductive overlayer, such as sputter-coated gold.

The fabricated NLO film must have a non-centrosymmetric alignment of the dipolar segments throughout the bulk of the polymer film. This is achieved by poling the film, or applying an electric field across the film. In corona poling, the field results form a discharge between a wire, such as tungsten, suspended above the film and a grounded heater block. The corona poling technique is described further by M. A. Mortazavi et al., *J. Opt. Sc. Am. B* 6 (1989). In parallel plate poling a voltage is applied across the two electrode layers. In both procedures a voltage is applied at elevated temperatures, near the polymer $T_g$ (approximately 5° to 10° C. above the onset of $T_g$ as measured by DSC). The field is left on for at least a few minutes and the sample cooled with the field on to maintain the orientation of the dipolar segments.

Another method of orientation of the thermoset polymer of the present invention for producing nonlinear optical materials includes polymerizing the prepolymer of a thermoset polymeric composition of the invention while the prepolymer is under an electric field such that the nonlinear optical moieties are aligned in the electric field before complete polymerization of the prepolymer takes place. This method of orientation will produce less stress on the ultimate polymer network than if the electric field is applied after the NLO moieties are incorporated into the backbone of the polymer.

The oriented polymeric compositions of the invention can be prepared by substantially simultaneously applying an external field and thermally annealing the reaction product of at least one compound of the invention corresponding to Formula I or to Formula II with at least one compound capable of copolymerizing therewith for a period of time sufficient to form a composition having nonlinear optical properties. This process for producing a nonlinear optical polymeric film comprises poling the film to orient the NLO moieties as described above, lowering the temperature to 10° to 50° C. below the glass transition temperature, and annealing for a period of time whereby a stable NLO polymeric film is obtained. This "annealing" step is carried out so as to cause a reduced free volume in the film and thus less room for NLO moieties to randomly reorient themselves which lead to a decrease in the NLO signal. Thus, this annealing process during the polymer orientation may advantageously improve the stability of the polymer. A specific example illustrating the advantages of thermally annealing and poling the polymeric film is set forth below.

The oriented film fabricated from the polymers of this invention can be characterized for their NLO activity by a Maker Fringe Rotation Second Harmonic Generation Technique which is well known to those skilled in the art. See for example, Singer et al., *Appl. Phys. Lett.*, 49, (1986) 2448–250.

The oriented polymeric film is used as a nonlinear optical medium in Mach-Zehnder intensity modulators, directional couplers, switches, frequency stabilizers, optical parametric devices, phase modulators, and passive waveguiding devices, as described in T. A. Tumolillo, Jr., "Multilevel registered polymeric Mach-Zehnder Intensity modulator array", *Applied Physics Letters*, 62(24), 14 Jun. 1993, U.S. Pat. No. 5,119,228, and G. R. Mohlmann et al., *Nonlinear Optical Properties of Organic Materials III*, SPIE Vol. 1337, (1990), the relevant portions of which are incorporated herein by reference.

The following preferred specific embodiments are to be construed as merely illustrative, and not limitative of the scope of the present invention in any way whatsoever. In the following examples, all temperatures are set forth uncorrected in degree Celsius; unless otherwise indicated, all parts and percentages are by weight.

EXAMPLE 1

5-(3-Hydroxy-4-methoxyphenyl)-3-(3-hydroxy-4-methoxystyryl)-1-(4-nitrophenyl)-4,5-dihydropyrazole (I)

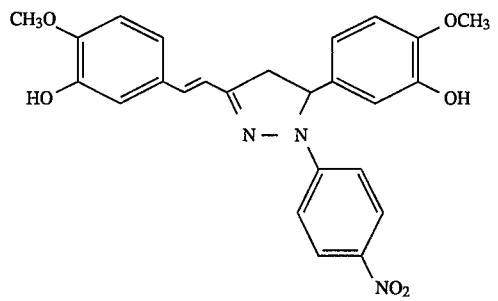

To a stirred mixture of 1,5-bis(3-hydroxy-4-methoxyphenyl)-1,4-pentadien-3-one (29.6 g, 90.8 mmol), absolute ethanol (220 mL), and 4-nitrophenylhydrazine (16.8 g, 100 mmol for 90 percent purity, 10 percent water) was added conc. HCl (20 mL), and the mixture was stirred and heated at reflux for 24 hours. The mixture was then stirred at room temperature for 16 hours, and the orange crystals that formed were removed by filtration. The product was washed with ethanol and hexane, and dried in a vacuum oven at 90°–100° C. for 12 hours. The product was obtained as orange-red microcrystals (37.2 g, 97.4 percent yield) mp 215°–217° C.; $^1$H NMR (DMSO-d6) δ9.09 (s, 2H), 8.05 (d, 2H, J=9.5 Hz), 7.06–6.61 (m, 10H), 5.52 (dd, 1H, J1=11.6 Hz, J2=4.1 Hz,), 3.80 (s, 3H), 3.76 (m, 1H), 3.73 (s, 3H), and 3.07 (m, 1H).

EXAMPLE 2

1,4-Bis[5-{3-(4-hydroxy-3-methoxyphenyl)-1-(4-nitrophenyl)}pyrazolinyl]benzene (II)

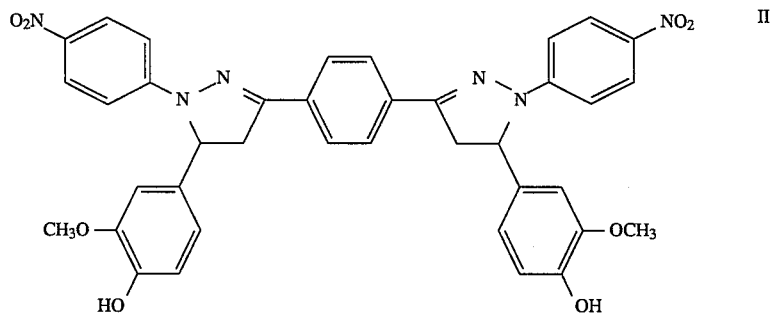

To a stirred mixture of the bis-ketone obtained by the base-catalyzed reaction between terephthal-aldehyde and acetovanillone (43 g, 0.1 mol), acetic acid (500 mL) and 4-nitrophenylhydrazine (42.1 g, 0.25 mol for 90 percent purity with 10 percent water) was added conc. HCl (20 mL). The mixture was heated and stirred under reflux for 3 hours. After cooling, the yellow precipitate was filtered, and the crude material was dissolved in 700 ml of hot DMF, filtered and cooled to room temperature. Addition of 1.2 liter of ethanol gave 43.5 g of the title compound as amorphous, yellow powder; Yield: 62 percent; mp 309°–311° C. The complex 1H NMR spectrum suggests that a mixture of diastereomers has been obtained.

EXAMPLE 3

1,3-Bis[5-{3-(4-hydroxy-3-methoxyphenyl)-1-(4-nitrophenyl)}pyrazolinyl]benzene (III)

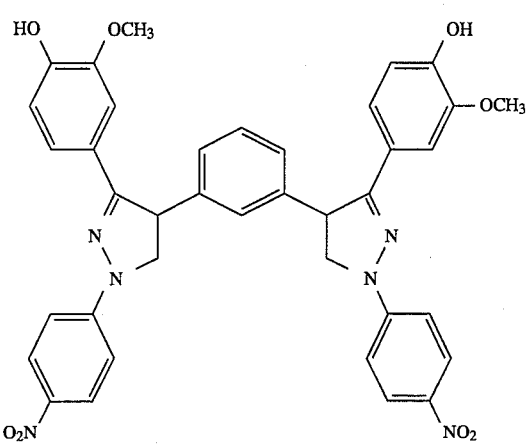

TABLE 1

| Compound (Solvent) | $\lambda_{max}$(nm) | $\mu\beta_{1064}$[1] | $\epsilon_{532}$[2] | $\mu\beta_{1579}$[1] | $\epsilon_{790}$[2] |
|---|---|---|---|---|---|
| I (THF) | 418 | 1537 | 21.4 | 526 | 0.19 |
| II (DMF) | 434 | 4035 | 682 | 1191 | 0.65 |
| III (DMF) | 427 | n.a. | n.a. | 496 | 0.38 |

[1]$10^{-48}$ esu?
[2]liter mole$^{-1}$ cm$^{-1}$

EXAMPLE 4

5-(3-(2,3-Epoxypropoxy)-4-methoxyphenyl)-3-(3-(2,3-epoxypropoxy)-4-methoxystyryl)-1-(4-nitrophenyl)-4,5-dihydropyrazole (IV)

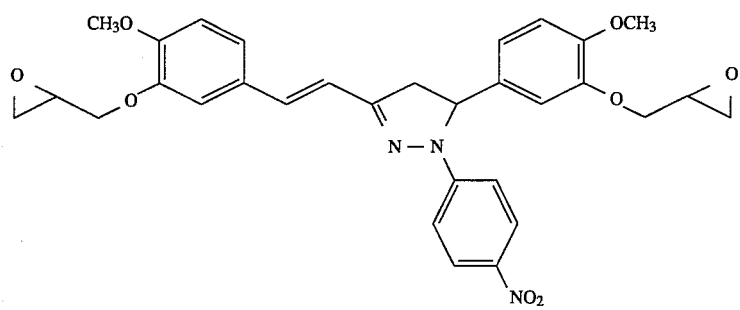

The meta-isomer of the above bis-pyrazoline was obtained as in Example 2 except that isophthalaldehyde was used in place of terephthalaldehyde, and was obtained as a yellow-orange amorphous powder in 53 percent yield, mp 265°–268° C. The 1H NMR spectrum was consistent with the assigned structure.

Measurements of Monomer NLO Activity by Electric Field Induced Second Harmonic Generation (EFISH)

The second order NLO activities of the compounds I–III were determined in solution using the Electric Field Induced Second Harmonic generation (EFISH) technique (see B. F. Levine and C. G. Bethea, *J. Chem. Phys.*, 63, 2666, 1975). A pulsed voltage of 5 kV was applied to electrodes in a solution cell with 2 mm electrode separation. The 5 kV pulses were synchronized with the firing of the laser (25 Hz). The input and output windows were sandwiched between the electrodes to achieve a wedge angle of 3.08° across the cell. The second harmonic generation (SHG) signal created by the solution was detected at a photomultiplier and was measured at a range of solution concentrations and normalized to the signal from a quartz reference wedge. The $\mu\beta$ product for the test molecule was determined from the SHG data as described by Levine and Bethea, supra. The excitation wavelength used was 1064 nm from a Quanta-Ray DCR-2a Nd$^{+3}$/YAG laser, or 1579 nm by Raman shifting (in H$_2$ gas at 400 psi) the 532 nm frequency doubled (using a KDP crystal) output of the same laser. Results for the measurement of $\mu\beta$ are shown in Table 1, including the solvents used in the measurements.

A mixture of diphenol I (10.0 g, 21.7 mmol), epichlorohydrin (90 mL), and benzyltrimethylammonium chloride (0.15 g, 0.8 mmol) was stirred at 85° C. for 16 hours. The mixture was cooled to 0° C. (ice/water bath) and sodium hydroxide (2 mL of a 50 percent aqueous solution) was added. The mixture was allowed to warm to room temperature and was stirred overnight. The mixture was diluted with dichloromethane and was washed with water. The organic layer was removed and dried over anhydrous magnesium sulfate, which was removed by filtration. Removal of solvents gave product as a red, crystalline solid. The product was purified by recrystallization from a hot chloroform/methanol mixture. The product was dried in a vacuum oven at 75° C. for 3 hours. Obtained 9.3 g of red, crystalline product (75 percent yield). Epoxy equivalent weight (e.e.w.) was determined by titration to be 304.61 g/equivalent epoxide (calculated e.e.w. 286.80 g/equivalent epoxide). $^1$H NMR (d$_6$-DMSO, 300 MHz) d 8.05 (d, J=9.5 Hz, 2H), 7.34–6.67 (m, 1OH), 5.58 (d, J=9.2 Hz, 1H), 4.39 (d, J=11.5 Hz, 1H), 4.28 (m, 1H), 3.80 (s, 3H), 3.73 (s, 3H), 3.10 (d, J=17.6 Hz, 1H), 2.89–2.68 (m, 3H). $^{13}$C NMR (d$_6$-DMSO) d 115.39, 149.73, 148.44, 147.85, 137.68, 136.56, 133.29, 128.87, 125.72, 121.76, 118.38, 117.90, 112.51, 111.82, 111.24, 110.52, 69.85, 61.71, 55.48, 49.73, 49.62, 43.80, 42.09.

EXAMPLE 5

1,4-Bis[5-{3-(4-(1,2-epoxypropoxy)-3-methoxyphenyl)-1-(4-nitrophenyl)}pyrazolinyl]benzene (V)

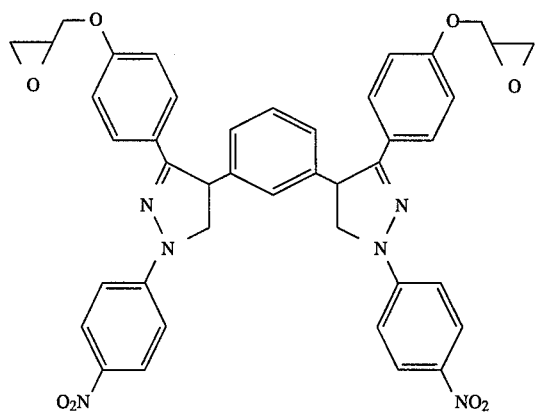

Compound V was prepared in the manner described above, using compound III as the precursor diphenol, and was obtained as an amorphous glass in 89 percent yield. Epoxy equivalent weight (e.e.w.) determined by titration was 411.45 g/equivalent epoxide (calculated e.e.w. 376.40 g/equivalent epoxide). $^1$H NMR (d$_6$-DMSO) d 7.87 (m, 2H), 7.66 (m, 2H), 7.37 (m, 1H), 7.21 (m, 1H), 7.06–6.90 (m, 5H), 5.64 (d, J=11.1Hz, 1H), 4.40 (d, J=11.4 Hz, 1H), 3.91 (m, 2H), 3.39 (m, 1H), 3.13 (d, J=17.1 Hz, 1H), 2.88 (m, 1H), 2.76 (m, 1H). $^{13}$C NMR (d$_6$-DMSO) 155.60, 152.33, 148.01, 141.76, 137.53, 130.17, 128.04, 125.39, 123.99, 123.88, 122.90, 114.69, 111.60, 79,14, 69.05, 61.96, 49.59, 43.74, 43.05.

EXAMPLE 6

Poly(hydroxy ether) Oligomer from Diglycidyl Ether (IV) and Diphenol I (VI)

A 100 mL minireactor, equipped with mechanical stirrer, nitrogen inlet, and condenser, was charged with diglycidyl ether IV (7.247 g, 11.93 mmol, 2 equiv/diphenol, 303.76 g/equivalent e.e.w.), diphenol I (2.753 g, 5.97 mmol), ethyltriphenylphosphonium iodide (0.031 g), and 2-methoxypropanol (25 mL). The mixture was heated to reflux under nitrogen for 24 hours, at which time DMF (25 mL) was added. The resulting solution was poured into water (700 mL), the precipitate was collected by suction filtration, and the product was dried in a vacuum oven at 70° C. overnight. Obtained 9.5 g product (95 percent yield). $^1$H and $^{13}$C NMR spectra were consistent with the expected structure.

EXAMPLE 7

Random Co-poly(carbonate) of Bisphenol A and I (BA/I PC)

A 0.5 L 4-neck roundbottom flask equipped with a thermometer, condenser, phosgene/nitrogen inlet, and a paddle stirrer connected to a Cole Parmer servodyne was charged with bisphenol A (6.16 g, 0.027 mol), diphenol I (12.44 g, 0.027 mol), pyridine (11.1 g, 0.140 mol) and CH$_2$Cl$_2$ (167 mL). The mixture was stirred at 250 rpm with a slow nitrogen purge and phosgene (5.9 g, 0.06 mol) was bubbled into the reaction mixture over 35 minutes, resulting in a viscous red-orange mixture. The reaction mixture was worked up by adding methanol (5 mL), a solution of 5 mL of conc. HCl in 40 mL water, and 30 mL of CH$_2$Cl$_2$. After stirring for 15 minutes at 200 rpm, the mixture was transferred to a separatory funnel. The CH$_2$Cl$_2$ layer was separated and the copolycarbonate was isolated by adding the CH$_2$Cl$_2$ solution to a solution of 0.2 L acetone and 2.0 L hexane in a high speed blender. The precipitate was collected by suction filtration and washed consecutively in the blender with a solution of 20 mL of conc. HCl and 2.0 L methanol, 2.0 L water, 2.0 L water, 2.0 L methanol, and a solution of 0.2 L acetone and 2.0 L hexane. The filtered product was dried in a hood overnight and then dried for 48 hours in a vacuum oven at 110° C. The resulting copolycarbonate weighed 18.2 g, had an inherent viscosity (IV) of 0.35 dL/g (determined in CH$_2$Cl$_2$ at 0.5 g/dL and 25° C.), and an extrapolated onset glass transition temperature (Tg) of 214° C. (determined by DSC at a scan rate of 20° C./min). The $^1$H NMR (CDCl$_3$) spectrum was consistent with the expected structure:

EXAMPLE 8

Random Co-poly(carbonate) of Bisphenol A and II (80/20) (BA/II 80/20 PC)

The general synthetic procedure of Example 7 was followed to prepare a bisphenol A/II (80/20 molar ratio) copolycarbonate which had an IV of 0.33 dL/g (CH$_2$Cl$_2$, 0.5 g/dL, 25° C.) and a Tg of 180° C.

EXAMPLE 9

Random Co-poly(carbonate) of Tetrachlorobisphenol A and I (TCBA/I PC)

The general synthetic procedure of Example 7 was followed to prepare a tetrachlorobisphenol A/I copolycarbonate which had an IV of 0.24 dL/g (CH$_2$Cl$_2$, 0.5 g/dL, 25° C.) and a Tg of 230° C.

EXAMPLE 10

Poly(hydroxy ether) from Bisphenol A Diglycidyl Ether and I (BA/I PHE)

Diphenol I (6.93 g, 15.0 mmol, 30.0 mmol phenolic groups), bisphenol A diglycidyl ether (5.25 g, 30.57 mmol epoxide, EEW=171.7 g/equivalent weight epoxide), and propylene glycol monophenyl ether (10 mL) were added to a 100 mL polymerization reactor which was then fitted with a thermometer, overhead mechanical stirrer, and nitrogen inlet and outlet adapters. The mixture was heated to 140° C. and 15 drops of 70 percent ethyltriphenylphosphonium acetate in methanol were added. The temperature of the reaction mixture rose to 165° C. over 10–15 minutes and was maintained at 160°–165° C. for 30 minutes as the solution became moderately viscous. No further viscosity increase was observed after 45 minutes. The solution was then diluted to a volume of 75 mL with DMF. The solution was precipitated into a solution of 3/1 methanol/water (400 mL). The product was washed with methanol (400 mL) and water (400 mL) in a high speed blender. The red/orange powder was collected via filtration, air dried, and then redissolved in THF (100 mL). The polymer was precipitated a second time as described previously. After drying in vacuo at 80° C. for 24 hours, 11.2 g of orange powder was obtained with an IV of 0.25 dL/g (DMF, 25.0° C.) and an onset T$_g$ of

150° C.

EXAMPLE 11

Poly(hydroxy ether) from Bisphenol A Diglycidyl Ether and II (BA/II PHE)

The general experimental procedure of Example 10 was followed to prepare a poly(hydroxy ether) using bisphenol A diglycidyl ether and diphenol II, to yield a product with an IV of 0.19 dL/g (DMF, 25° C., 0.5 g/dL), and a $T_g$ of 173° C.

EXAMPLE 12

Poly(hydroxy ether) from 9,9-Bis-(4-(2,3-epoxypropoxy)phenylfluorene) and I (BHPF/I PHE)

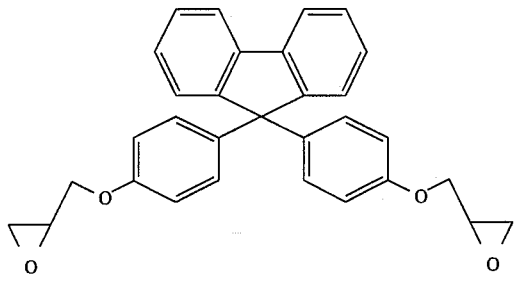

The general experimental procedure of Example 10 was followed to prepare a poly(hydroxy ether) using 9,9-bis(4-(2,3-epoxypropoxy)phenyl)fluorene and diphenol I, to yield a product with an IV of 0.53 dL/g (DMF, 25° C., 0.5 g/dL), and a $T_g$ of 195° C.

EXAMPLE 13

Poly(hydroxy ether) from Bisphenol A Diglycidyl Ether and II (75/25) (BA/II 75/25 PHE)

The general experimental procedure of Example 10 was followed to prepare a poly(hydroxy ether) using bisphenol A diglycidyl ether, bisphenol A, and diphenol I with a 1:1 mole ratio of diphenols, to yield a product with an IV of 0.35 dL/g (DMF, 25° C., 0.5 g/dL), and a $T_g$ of 145° C.

Measurement of NLO Activity of Films

This describes the representative measurement of the second-order nonlinear optical coefficient ($d_{33}$) for parallel plate poled and corona poled films of the polymers described above in Example 7.

A film (1.08 μm thickness) was prepared by spin-coating onto an ITO coated glass slide from a 15 percent weight/volume solution of BA/II 80/20 PC in cyclopentanone. The film was dried at 20° C. for 18 hours in air, 100° C. for 2 hours in airy 100° C. for 2 hours under vacuum and then at 180° C. for 1 hour under vacuum. The film was coated with a 14 nm Au strip electrode. A DC bias of 33 V was applied to the ITO(+) and Au(−) electrodes. The film was heated to from 30°–190° C. and 190°–30° C. at a rate of 2° C./minute. The $d_{33}$ value was determined by second harmonic generation measurements using the Maker Fringe rotation method (see K. D. Singer et al., *Appl. Phys. Lett.*, 49 248, 1986). A fundamental wavelength of 1064 nm was used. A y-cut quartz crystal ($d_{11}$=1.2×10$^{-9}$ esu) was used as a reference. A $d_{33}$ value of 3.7×10$^{-9}$ esu was determined assuming refractive index values of 1.5929 at 532 nm and 1.5677 at 1064 nm.

A corona poled sample of this polycarbonate was processed similarly. A film (1.17 μm thickness) of this polycarbonate was spin-coated onto a glass substrate and dried as described above. The film was placed on a resistively heated block with a tungsten wire 15 mm above the sample. A voltage of 4.18 kV, current of 1.0 mA and maximum poling temperature of 188° C. was used. Here the sample was rapidly heated to the poling temperature of 187° C., soaked for 15 minutes and let cool to room temperature. A $d_{33}$ value of 7.3×10$^{-9}$ esu was determined.

Table II summarizes the $d_{33}$ values measured for some of the polymers of this invention. In most cases the samples were ramped rapidly to a maximum poling temperature (5°–10° C. above the Tg), soaked for 15 minutes and allowed to cool with the field on.

TABLE II

| Example | AR | | | | | Type[d] | ηinh (dL/g) | Tg (°C.) | $d_{33}$[e] (× 10$^{-9}$ esu) |
|---|---|---|---|---|---|---|---|---|---|
| | BA[a] | BHPF[b] | TCBA[c] | I | II | | | | |
| 7 | 1 | — | — | 1 | — | PC | 0.35 | 214 | 29[f] |
| 8 | 4 | — | — | — | 1 | PC | 0.33 | 180 | 7[f] |
| 9 | — | — | 1 | 1 | — | PC | 0.24 | 230 | 8 |
| 10 | 1 | — | — | 1 | — | PHE | 0.25 | 150 | 19 |
| 11 | 1 | — | — | — | 1 | PHE | 0.19 | 173 | 18 |
| 12 | — | 1 | — | 1 | — | PHE | 0.53 | 195 | 21 |
| 13 | 3 | — | — | 1 | — | PHE | 0.35 | 145 | 16 |

[a]BA- bisphenol A.
[b]BHPF- 9,9-bis(4-hydroxyphenyl)fluorene.
[c]TCBA-tetrachlorobisphenol A.
[d]PC- poly(carbonate), PHE- poly(hydroxy ether).
[e]parallel plate poled with an applied field of 0.5M V/cm.
[f]corona poled.

EXAMPLE 14

To a mixture of IV (1.50 g, 0.0048 eq) and Tactix™ 742, commercially available from The Dow Chemical Company (0.62 g, 0.0039 eq) in dimethylacetamide (DMAc) (10 mL) was added 4,4'-diaminodiphenyl sulfone (DADS) (0.55 g, 0.0089 eq). Nitrogen was bubbled through this mixture at room temperature for 30 minutes, which was then heated at 160° C. for about 5 hours. The mixture became more viscous as the solution cooled to room temperature.

Films were spin coated at 1,000 rpm for 40 seconds and allowed to air dry for several days. The films were further dried in a nitrogen purged oven for 3 hours at 80° C., 2 hours at 110° C. and 2.5 hours at 140° C. The resulting films were approximately 1.4 μm thick.

The films were simultaneously poled and cured with an applied field of 50 V/μm at 180° C. for 2 hours, ramped to 220° C. over 1 hour, held at 220° C. for 3 hours, and ramped to 180° C. over 30 minutes. The material had a Tg of 250° C., and a $d_{33}$ of $51 \times 10^{-9}$ esu at 1064 nm when measured as described above.

EXAMPLE 15

Compound IV (1.53 g, 0.0049 eq) and D.E.R.™ 332, commercially available from The Dow Chemical Company (1.54 g, 0.0089 eq) were added to an aluminum pan and heated to 180° C. in an air oven to make a homogeneous mixture. DADS (0.88 g, 0.014 eq) was added to this hot mixture, which was heated for an additional approximately 15 minutes at 180° C. This mixture was then cooled to room temperature to yield a solid prepolymer that was soluble in organic solvents.

Films were prepared by dip coating from a propylene glycol methyl ether acetate/THF solution, and allowing the films to air dry for several days. The films were then dried in a nitrogen purged oven for 3 hours at 80° C., 2 hours at 110° C. and 2 hours at 140° C. The resulting films were about 2 to 4 μm thick.

The films were simultaneously poled and cured with an applied field of 50 V/μm at 180° C. for 2 hours, ramped to 220° C. over 1 hour, held at 220° C. for 3 hours. The material had a $T_g$ of 225° C., and a $d_{33}$ of $35 \times 10^{-9}$ esu at 1064 nm.

Stability of Thermoplastic Polymers

Two samples of Example 12 were taken for comparison to illustrate the thermal stability, and effect of annealing on the NLO activity of BHPF/II PHE.

One sample (A) was poled as described above by ramping at 2° C. per minute from 30° C. to 190° C. and 190° C. to 30° C. with an applied field of 0.3 MV/cm. Another sample (B) was poled by heating rapidly to 160° C., soaking at 160° C. for 30 minutes, soaking at 165° C. for 10 minutes, 180° C. for 15 minutes, 160° C. for 10 minutes, 150° C. for 30 minutes, ramped to 100° C. in 50 minutes and allowed to cool to room temperature while the field remained on. The $d_{33}$ values were calculated in arbitrary units as the square root of the SHG signal and normalized to the $d_{33}$ at 54.5° C. The annealed sample (B) has an onset of loss of SHG signal at a temperature of 181° C. The unannealed sample (A) has an onset of loss of SHG signal at a lower temperature (172° C.). This data shows that the annealed sample is more thermally stable than the unannealed sample. The SHG signal as a function of temperature is tabulated in Table III. The relative SHG signal is normalized relative to the initially obtained SHG signal.

TABLE III

| | SHG Signal as Function of Temperature | |
|---|---|---|
| | Relative SHG Signal | |
| Temperature °C. | Example 12 (A) | Example 12 (B) |
| 50 | 1.01 | 1.01 |
| 100 | 0.95 | 0.96 |
| 150 | 0.87 | 0.90 |
| 160 | 0.83 | 0.88 |
| 170 | 0.75 | 0.84 |
| 175 | 0.66 | 0.81 |

TABLE III-continued

| | SHG Signal as Function of Temperature | |
|---|---|---|
| | Relative SHG Signal | |
| Temperature °C. | Example 12 (A) | Example 12 (B) |
| 180 | 0.48 | 0.76 |
| 185 | 0.11 | 0.64 |
| 190 | — | 0.40 |
| 195 | — | 0.13 |

Stability of Thermoset Polymers

The long term thermal stability of the polymers of Examples 14 and 15 was evaluated by measuring the NLO activity coefficient $d_{33}$ as a function of time following 100° C. exposure in a recirculating air oven. The relative SHG values are tabulated as a function of temperature in Tables IV and V, respectively. The relative SHG signals are normalized relative to the initially obtained SHG signal. The results set forth in Tables IV and V indicate that the thermoset polymers are stable at 100° C. for over 110 days. The polymers retain about 65 percent of their original NLO activity at 100° C. for at least 100 days.

TABLE IV

| Isothermal Aging for Example 14 at 100° C. in Air | |
|---|---|
| Time at 100° C. in Air (days) | Relative SHG Signal ($d_{33} \times 10^{-9}$ esu)ⁿ |
| 0 | 1.0 |
| 1 | 1.0 |
| 4 | 1.08 |
| 7 | 1.0 |
| 110 | 0.657 |
| 200 | 0.54 |

TABLE V

| Isothermal Aging for Example 15 at 100° C. in Air | |
|---|---|
| Time at 100° C. in Air (days) | Relative SHG Signal ($d_{33} \times 10^{-9}$ esu)ⁿ |
| 0 | 1.0 |
| 5 | 0.91 |
| 13 | 0.94 |
| 20 | 0.94 |
| 23 | 0.77 |
| 123 | 0.685 |
| 213 | 0.6 |

What is claimed is:

1. A nonlinear optical medium comprising an oriented polymeric composition comprising moieties obtained by condensation polymerization of a compound corresponding to the Formula:

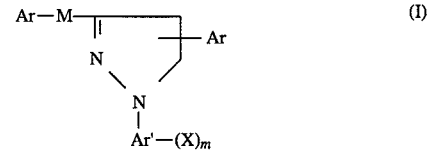

(I)

or to the Formula:

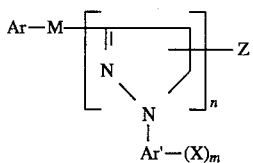

wherein Ar is independently at each occurrence an aromatic hydrocarbyl radical substituted with from zero to three polymerizable OR groups and optionally substituted with inert substituents, R is a hydrogen, an epoxy, or an alkylepoxy; Ar' is an aromatic hydrocarbyl radical containing up to 30 non-hydrogen atoms; X is an electron withdrawing group; M is a covalent bond or a divalent conjugated group; Z is a divalent or a trivalent aromatic carbocyclic radical or a substituted divalent or a trivalent aromatic carbocyclic radical containing up to 30 non-hydrogen atoms, or a covalent bond; n is 2 or 3; and m is an integer from 1 to 3; provided that there are at least two aromatically substituted OR groups present in the compound.

2. The oriented polymeric composition of claim 1, wherein the electron withdrawing group is selected from the group consisting of: $NO_2$, $-SO_2R''$, $-SO_2CH_2F$, $-SO_2CHF_2$, $-SO_2CF_3$, $-S(NSO_2CF_3)CF_3$, $-CF_3$, $-CO_2R''$, $-COCF_3$, cyano, cyanovinyl, dicyanovinyl, and tricyanovinyl, wherein R'' is hydrogen or a $C_1$ to $C_{20}$ hydrocarbyl radical.

3. The oriented polymeric composition of claim 1, wherein M is selected from the group consisting of $-C=C-$, $-CR''=CR''-$, $-CR''=CR''-CR''=CR''-$, $-CR''=N-$, $-N=CR''-$, and $-N=N-$, wherein R'' is as defined in claim 2.

4. The oriented polymeric composition of claim 1, wherein the inert substituent is R' or OR', wherein R' is a $C_1$ to $C_{20}$ hydrocarbyl radical.

5. The oriented polymeric composition of claim 1, wherein Ar is independently at each occurrence selected from the group consisting of:

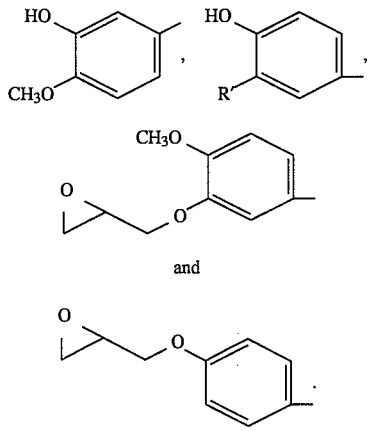

6. The oriented polymeric composition of claim 5, wherein the polymer further comprises at least one other monomer copolymerizable therewith.

7. The oriented polymeric composition of claim 5, wherein the polymer is a reaction product of the compound of Formula (I) or Formula (II) with at least one curing agent capable of reacting with the compound.

8. The oriented polymeric composition of claim 6 wherein the polymer is an oligomer comprising moieties derived from 5-(3-hydroxy-4-methoxyphenyl)- 3-(3-hydroxy-4-methoxystyrol)-1-(4-nitrophenyl)pyrazoline and 5-(3-(2,3-epoxyprpoxy)-4-methoxyphenyl)- 3-(3-(2,3-epoxypropoxy)-4-methoxystyryl)-1-(4 -nitrophenyl)-pyrazoline.

9. The oriented polymeric composition of claim 6 wherein the polymer is a copolycarbonate comprising 5-(3-hydroxy-4-methoxyphenyl)-3-(3-hydroxy- 4-methoxystyrol)-1-(4-nitrophenyl)-pyrazoline and bisphenol A or tetrachlorobisphenol A.

10. The oriented polymeric composition of claim 6 wherein the polymer is a copolycarbonate comprising 1,4-bis[5-{3-(4-hydroxy-3-methoxyphenyl)- 1-(4-nitrophenyl)}pyrazolinyl}-benzene and bisphenol A.

11. The oriented polymeric composition of claim 6 wherein the polymer is a poly(hydroxy ether) comprising 5-(3-hydroxy-4-methoxyphenyl)-3-(3-hydroxy- 4-methoxystyrol)-1-(4-nitrophenyl)-pyrazoline and diglycidyl ether of bisphenol A or 9,9-bis-( 4-(2,3-epoxypropoxy)phenylfluorene.

12. The oriented polymeric composition of claim 6 wherein the polymer is a poly(hydroxy ether) comprising 1,4-bis[5-{3-(4-hydroxy-3-methoxyphenyl)- 1-(4-nitrophenyl)}-pyrazolinyl}benzene and diglycidyl ether of bisphenol A.

13. The oriented polymeric composition of claim 7 wherein the curing agent is selected from the group consisting of 4,4'-diaminodiphenylsulfone, p-nitroaniline, methyl nitroaniline, nitrobenzylamine, bisphenol A, and tetrabromobisphenol A.

14. The oriented polymeric composition of claim 13, comprising the reaction product of 5-(3-(2,3-epoxypropoxy)-4-methoxyphenyl)- 3-(3-(2,3-epoxypropoxy)-4-methoxystyryl)- 1-(4-nitrophenyl)-4,5-dihydropyrazole with 4,4'-diaminodiphenylsulfone.

15. A process of preparing an oriented polymeric composition comprising applying an external field to the polymeric compositions comprising moieties obtained by condensation polymerization of a compound corresponding to the Formula:

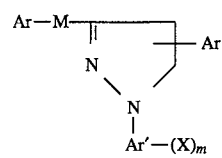

or to the Formula:

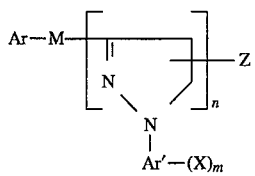

wherein Ar is independently at each occurrence an aromatic hydrocarbyl radical substituted with from zero to three polymerizable OR groups and optionally substituted with inert substituents, R is a hydrogen, an epoxy, or an alkylepoxy; Ar' is an aromatic hydrocarbyl radical containing up to 30 non-hydrogen atoms; X is an electron withdrawing group; M is a covalent bond or a divalent conjugated group; Z is a divalent or a trivalent aromatic carbocyclic radical or a substituted divalent or a trivalent aromatic carbocyclic radical containing up to 30 non-hydrogen atoms, or a covalent bond; n is 2 or 3; and m is an integer from 1 to 3; provided that there are at least two aromatically substituted OR groups present in the compound.

16. A process for preparing an oriented polymeric composition comprising substantially simultaneously applying an external field and thermally annealing the reaction product of at least one compound corresponding to the Formula:

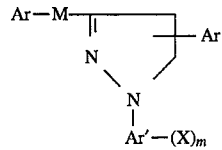

or to the Formula:

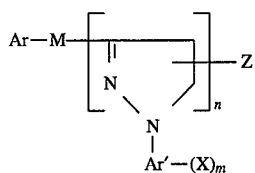

wherein Ar is independently at each occurrence an aromatic hydrocarbyl radical substituted with from zero to three polymerizable OR groups and optionally substituted with inert substituents, R is a hydrogen, an epoxy, or an alkylepoxy; Ar' is an aromatic hydrocarbyl radical containing up to 30 non-hydrogen atoms; X is an electron withdrawing group; M is a covalent bond or a divalent conjugated group; Z is a divalent or a trivalent aromatic carbocyclic heterocyclic radical, or a substituted divalent or a trivalent aromatic carbocyclic or heterocyclic radical containing up to 30 non-hydrogen atoms, or a covalent bond; n is 2 or 3 and m is an integer from 1 to 3; provided that there are at least two aromatically substituted OR group present in the compound; with at least one curing agent capable of reacting with the compounds.

17. A device comprising an oriented polymeric composition comprising moieties obtained, by condensation polymerization of a compound corresponding to Formula:

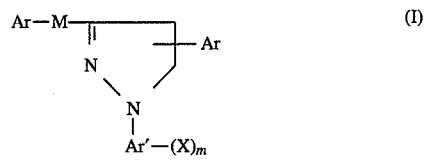

or to the Formula:

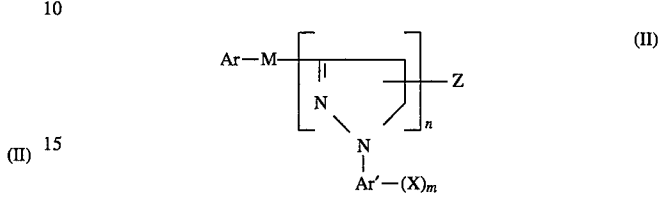

wherein Ar is independently at each occurrence an aromatic hydrocarbyl radical substituted with from zero to three polymerizable OR groups and optionally substituted with inert substituents, R is a hydrogen, an epoxy, or an alkylepoxy; Ar' is an aromatic hydrocarbyl radical containing up to 30 non-hydrogen atoms; X is an electron withdrawing group; M is a covalent bond or a divalent conjugated group; Z is a divalent or a trivalent aromatic carbocyclic radical or a substituted divalent or a trivalent aromatic carbocyclic or heterocyclic radical containing up to 30 non-hydrogen atoms, or a covalent bond; n is 2 or 3; and m is an integer from 1 to 3; provided that there is at least one aromatically substituted OR group present in the compound.

18. The process of claim 16 wherein the curing agent is selected from the group consisting of 4,4'-diaminodiphenylsulfone, p-nitroaniline, methyl nitroaniline, nitrobenzylamine, bisphenol A, and tetrabromobisphenol A.

19. The process of claim 18, comprising the reaction product of 5-(3-(2,3-epoxypropoxy)-4-methoxyphenyl)-3-(3-(2,3-epoxypropoxy)- 4-methoxystyryl)-1-(4-nitrophenyl)-4,5-dihydropyrazole with 4,4'-diaminodiphenylsulfone.

* * * * *